(12) United States Patent
Loria (10) Patent No.: US 9,877,835 B1
(45) Date of Patent: Jan. 30, 2018

(54) FLACCID PENILE INSERT (71) Applicant: Victor Loria, Doral, FL (US)

(72) Inventor: Victor Loria, Doral, FL (US)

( * ) Notice: Subject to any disclaimer, the term of this patent is extended or adjusted under 35 U.S.C. 154(b) by 0 days.

(21) Appl. No.: 15/678,418

(22) Filed: Aug. 16, 2017

Related U.S. Application Data

(60) Provisional application No. 62/442,664, filed on Jan. 5, 2017.

(51) Int. Cl.
*A61F 5/00* (2006.01)
*A61F 2/26* (2006.01)
(52) U.S. Cl.
CPC ........ *A61F 2/26* (2013.01); *A61F 2230/0004* (2013.01)
(58) Field of Classification Search
CPC .......................................................... A61F 2/26
USPC ..................................................... 600/38–41
See application file for complete search history.

(56) References Cited

U.S. PATENT DOCUMENTS

| 5,921,246 A | * | 7/1999 | Cho | A61B 90/00 128/898 |
| 6,015,380 A | * | 1/2000 | Subrini | A61F 2/26 600/38 |
| 7,806,821 B2 | * | 10/2010 | Kim | A61F 2/26 600/38 |
| 2006/0096603 A1 | * | 5/2006 | Choi | A61F 2/26 128/898 |

* cited by examiner

*Primary Examiner* — John Lacyk (57) ABSTRACT

A penile insert device effective to prevent retraction of the penis and to increase the length of a penis in its flaccid or erect state. An elongated body of the penile insert device can have a proximal end, a distal end, a first side edge, a second side edge, a top surface, and a bottom surface. Each of the first and second side edges is formed by a plurality of alternating lateral plateaus and lateral valleys. The lateral plateaus are smoothly connected to adjacent lateral plateaus by the lateral valleys. The lateral valleys of the first side edge is staggered with respect to the lateral valleys of the second side edge such that the lateral plateaus and valleys of the first lateral side and the lateral plateaus and valleys of the second side edge form a zigzag pattern in the body.

20 Claims, 6 Drawing Sheets

FLACCID PENILE INSERT

CROSS REFERENCE

This application claims priority to U.S. Patent Application No. 62/442,664, filed Jan. 5, 2017, the specification(s) of which is/are incorporated herein in their entirety by reference.

FIELD OF THE INVENTION

The present invention relates penile inserts, namely to penile inserts that can increase the length of a penis in its flaccid state, and possibly increase the length of a penis in its erect state.

BACKGROUND OF THE INVENTION

The flaccid penis retracts under certain circumstances, perhaps most notably in cold environments, upon vigorous exercise, and upon elicitation of the "fight or flight" response. Penile retraction is due to the contraction of the dartos muscle and elastic fibers in the penile tissue. Retraction of the penis results in a decrease in the apparent size of the penis, which can be a source of embarrassment to one undergoing penile retraction, especially in gym locker rooms, public showers, and the like. Therefore, it is desirable to prevent penile retraction in order to not only avoid potential embarrassment, but to also improve confidence and self-esteem.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY OF THE INVENTION

It is an objective of the present invention to provide for penile inserts along with methods of use thereof for increasing a length of a penis in its flaccid or erect state, as specified in the independent claims. Embodiments of the invention are given in the dependent claims. Embodiments of the present invention can be freely combined with each other if they are not mutually exclusive.

According to one embodiment, the subject disclosure features a penile insert device effective for increasing a length of a penis in its flaccid or erect state. The penile insert device may comprise an elongated body having a proximal end, a distal end, a first side edge, a second side edge, a top surface, and a bottom surface. Each of the first and second side edges is formed by a plurality of alternating lateral plateaus and lateral valleys. The lateral plateaus may be smoothly connected to adjacent lateral plateaus by the lateral valleys. The lateral valleys of the first side edge may be staggered with respect to the lateral valleys of the second side edge such that the lateral plateaus and valleys of the first side edge and the lateral plateaus and valleys of the second side edge form a zigzag pattern in the body.

According to another embodiment, each lateral plateau may comprise two rounded corners, each rounded corner smoothly transitioning the lateral plateau into a lateral valley. In some embodiments, a suture system may be disposed on each corner of the lateral plateau. The suture system may comprise a suture aperture disposed through the body from the top surface to the bottom surface, a suture groove disposed on the side edge and in alignment with the suture aperture, and a suture pocket disposed on the top surface adjacent to the suture aperture.

In some aspects, the device may be configured to be implanted into a penile shaft underneath a penile skin and sutured to a penile facial tissue layer so that the device can prevent or reduce shrinkage and elongate an appearance of the penis in its flaccid state, and can further elongate the appearance of the penis in its erect state. In one embodiment, the proximal end may be disposed near a pubic bone and the distal end may be disposed near a glans coronal rim of the penis. In another embodiment, when the device is sutured to the penile facial tissue layer, the suture may be looped around the suture aperture, facial tissue layer and side edge. The suture is disposed in the suture groove such that the suture is flushed with the side edge, and the suture is knotted into a suture knot that is then disposed in the suture pocket.

In further embodiments, the elongated body may have a plurality of widthwise trenches disposed on the top and bottom surfaces, and extending from the first side edge to the second side edge. A plurality of lengthwise trenches may be disposed on the top and bottom surfaces in a perpendicular orientation to the widthwise trenches.

One of the unique and inventive technical features of the present invention is the plurality of alternating lateral plateaus and lateral valleys making up the side edges and forming the zigzag pattern. Another unique and inventive technical feature is plurality of widthwise trenches and lengthwise trenches. Without wishing to limit the invention to any theory or mechanism, it is believed that these technical features of the present invention advantageously provides for a bendable device that can move with the movement of the penis without causing discomfort to the user. None of the presently known prior references or work has the unique inventive technical feature of the present invention.

BRIEF DESCRIPTION OF THE DRAWINGS

The features and advantages of the present invention will become apparent from a consideration of the following detailed description presented in connection with the accompanying drawings in which.

DESCRIPTION OF PREFERRED EMBODIMENTS

Following is a list of elements corresponding to a particular element referred to herein:
100 penile insert device
110 elongated body
112 proximal end
114 distal end
122 first side edge
124 second side edge
132 top surface
134 bottom surface
140 rounded tip
150 lateral plateaus
155 plateau corner
160 lateral valleys
170 suture system
172 suture aperture
174 suture groove
176 suture pocket
178 suture
192 widthwise trench
194 lengthwise trench As used herein, the term "proximal" refers to being situated near or towards the pubic area. The term "distal" refers to being situated away from the pubic area.

As used herein, the term "dorsal" refers to the top or upper surface or side, while the term "ventral" refers to the bottom or lower surface or side.

As known to one of ordinary skill in the art, the sagittal plane is an anatomical plane in the Y-Z dimension that divides the body into "left" and "right" parts or sides. As used herein, the term "left" refers to the left side of the body and the term "right" refers to the right side of the body.

The term "lateral" is defined as being parallel to or in the general direction of the surface of the body. The term "longitudinal" is defined as being normal to, or perpendicular, to the lateral direction.

The term "gradually" is defined as rising or descending at an even, moderate inclination. The term "smoothly" is defined as having an even surface or edge free from irregularities, sharpness (i.e. hard-angled corners), or roughness.

Referring now to FIG. 1-10, in one embodiment, the present invention features a penile insert device (100) effective for increasing a length of a penis in its flaccid or erect state. The penile insert device (100) may comprise an elongated body (110) having a proximal end (112), a distal end (114), a first side edge (122), a second side edge (124), a top surface (132) fluidly connecting said proximal end (112) to said distal end (114), and said first side edge (122) to said second side edge (124), and a bottom surface (134) fluidly connecting said proximal end (112) to said distal end (114), and said first side edge (122) to said second side edge (124). In some embodiments, the top surface (132) is convexed and the bottom surface (134) is concaved such that the body (110) has a curvature when viewed from the proximal or distal end. The curvature of the body (110) may be similar to a surface curvature of the penis, which is advantageous in that it mimics the substantially round shape of the penis, thereby maintaining the natural shape of the penis when the device (100) is implanted.

Figure 3:
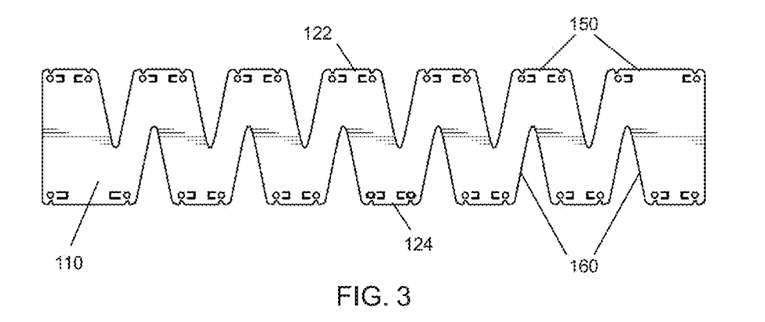
FIG. 3 shows a top view of a non-limiting embodiment of the present invention.

In one embodiment, each of the first and second side edges (122, 124) is formed by a plurality of alternating lateral plateaus (150) and lateral valleys (160). The lateral plateaus (150) may be smoothly connected to adjacent lateral plateaus (150) by the lateral valleys (160). In another embodiment, the lateral valleys (160) of the first side edge (122) are staggered with respect to the lateral valleys (160) of the second side edge (124) such that the lateral plateaus and valleys of the first side edge (122) and the lateral plateaus and valleys of the second side edge (124) form a zigzag pattern in the body (110).

Figure 4:
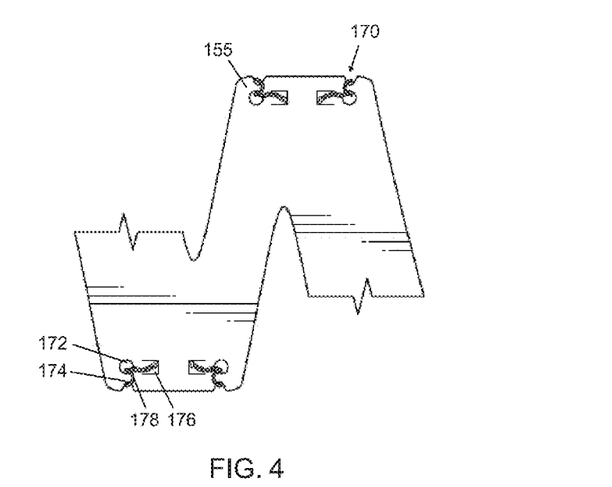
FIG. 4 shows a close-up view of the suture system of the penile insert.

In some embodiments, each lateral plateau (150) may comprise two rounded corners (155) that smoothly transition the lateral plateau (150) into a lateral valley (160). In other embodiments, a suture system (170) may be disposed on each corner (155) of the lateral plateau. The suture system (170) may comprise a suture aperture (172) disposed through the body (110) from the top surface (132) to the bottom surface (134), a suture groove (174) disposed on the side edge and in alignment with the suture aperture (172), and a suture pocket (176) disposed on the top surface (132) adjacent to the suture aperture (172). In further embodiments, the suture aperture (172) may further comprise a bevelled aperture edge. The bevelled aperture edges are advantageous in that they prevent "sawing" or cutting of the sutures that might result from friction between the sutures and a non-bevelled edge. The bevelled edges thus prevent ripping of the sutures that might otherwise occur without bevelled edges.

In some embodiments, the suture groove can provide a channel in which the sutures can rest against. Advantageously, this prevents body (110) from pressing the sutures into or rubbing the sutures against the various tissue layers of the penis, thereby preventing or reducing irritation to the penis. In other embodiments, the suture groove (174) may further comprise a bevelled suture groove edge. Advantageously, the suture grooves may be bevelled in order to prevent the sutures from fraying while in the suture grooves, which might otherwise occur with non-bevelled suture groove edges.

In one embodiment, the suture pockets are advantageous in that they provide a means to store the knotted ends of a tied suture and thus preventing the body (110) from pressing the sutures into or rubbing the sutures against the various tissue layers of the penis, thereby preventing or reducing irritation to the penis.

The device (100) may be sewn or attached to any tissue layer of the penis in order to function in accordance with the present invention. For example, the device may be sewn to the Buck's fascia and/or tunica albuginea to provide for an effective increase in flaccid penile length and for long term stability of the implanted device. However, other methods of attaching the device to the penis may be utilized, such as stapling, gluing, and the like.

In preferred embodiments, the device (100) may be configured to be implanted into a penile shaft of the penis and underneath a penile skin such that the proximal end (112) is disposed near a pubic bone and the distal end (114) is disposed near a glans coronal rim of the penis. In some embodiments, the suture system (170) is configured to retain a suture (178) that stitches the device (100) to penile tissue layer. For example, when attaching the device (100) to the penile tissue layer, the suture (178) is disposed through the suture aperture (172) and penile tissue layer, and then looped around the side edge. The suture (178) is preferably disposed in the suture groove (174) such that the suture (178) is flushed with the side edge. The suture is knotted into a suture knot, which is placed in the suture pocket (176).

Without wishing to limit the invention to a particular theory or mechanism, the device (100) may prevent or reduce shrinkage, and elongate the appearance of the penis in its flaccid state. In addition, the device (100) is capable of bending with the penis as it bends. Further still, the device (100) may elongate the appearance of the penis in its erect state.

In some embodiments, the top surface (132) may taper at the proximal and distal ends. In other embodiments, the top surface (132) may taper at the first and second side edges. In still other embodiments, the proximal and distal ends may have rounded tips (140). In further embodiments, the first and second side edges may have rounded tips (140). It is advantageous to round all corners, edges, and tips of the body in order to avoid any sharp tips, edges, or corners that would otherwise cause irritation or tearing of the penile skin or tissue.

In a preferred embodiment, the body (110) may be constructed from a semi-rigid, bendable silicone rubber material. The material may also be medical grade silicone rubber. The semi-rigid bendable material is advantageous in that allows for the device to bend with the penis while maintaining its structure. To illustrate, when the device is mounted, or sutured at each end, the penis may retract and if the material is too soft or pliable, the device may bow out and protrude, which would make the device visible through the penis skin. Further still, it is preferred that the material can stretch to accommodate a penis entering an erect state. In other embodiments, the use of medical grade silicone may allow for the penile insert device (100) to be used for the duration of the user's lifetime.

Figure 6:
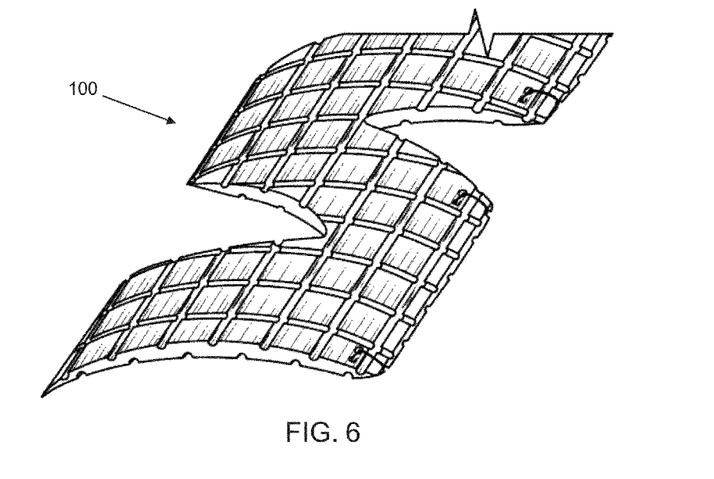
FIG. 6 shows a partial perspective view of an alternate embodiment of the penile insert.

In one embodiment, the body (110) may further comprise a plurality of widthwise trenches (192) disposed on the top and bottom surfaces, and extending from the first side edge (122) to the second side edge (124). In another embodiment, the body (110) may further comprise a plurality of lengthwise trenches (194) disposed on the top and bottom surfaces. The lengthwise trenches (194) may be perpendicular to the widthwise trenches (192).

In some embodiments, each widthwise trench (192) disposed on the top surface (132) may gradually widen midway between the first side edge (122) and the second side edge (124). In other embodiments, each widthwise trench (192) disposed on the bottom surface (132) may gradually narrow midway between the first side edge (122) and the second side edge (124).

In some embodiments, the penile insert may have a width of about 14-20 mm at its ends. In one embodiment, the penile insert may have a width of about 14 mm. In another embodiment, the penile insert may have a width of about 16 mm. In another embodiment, the penile insert may have a width of about 18 mm. In yet another embodiment, the penile insert may have a width of about 20 mm.

In some embodiments, the penile insert may have a length of about 3 to 6 inches from the proximal end to the distal end. In one embodiment, the penile insert may have a length of about 3-4 inches. In another embodiment, the penile insert may have a length of about 4-5 inches. In yet another embodiment, the penile insert may have a length of about 5-6 inches. This variance in length will accommodate for natural variances in penile length as well as providing a recipient of the penile insert device (100) with a variety of choices regarding a desired flaccid penile length.

In yet other embodiments, the penile insert may be manufactured to have an initial length of about 9-12 inches. The penile insert may then be cut down to size to fit each recipient individually and to a desired flaccid penile length. Without wishing to limit the invention to a particular theory or mechanism, the multiple suture systems allow for the insert to be cut to a desired length and still be able to be sutured at the distal and proximal ends.

Further still, in some embodiments, the multiple suture systems allow for the penile insert to be sutured at the distal and proximal ends, as well as at desired intervals or locations along the length of the penile insert, such as for example, at the midpoint of the penile insert. Without wishing to limit the invention to a particular theory or mechanism, this feature can prevent the penile insert form bowing outward if the flaccid penis is compressed (i.e. like the collapse of an accordion).

According to some embodiments, the suture aperture may have a diameter of about 0.5 to 1.5 mm. For example, the diameter of the suture aperture is about 1.5 mm. The suture aperture may be disposed at or near each corner of the plateau at a distance of about 1-2 mm away from the side edge of the insert and about 1-2 mm away from its neighboring valley. Preferably, the suture groove is disposed on the side edge of the insert such that it is aligned with the suture aperture. The suture groove and aperture essentially forms a bridge. In other embodiments, the suture pocket may be rectangular in shape. However, the suture pocket may be any suitable shape for holding the suture. In one embodiment, the suture pocket may be about 1-2 mm in width and 2-3 mm in length. Preferably, the suture pocket may be about 1-2 mm away from the side edge of the insert. When the penile insert is implanted into a penis, the insert is secured to penis via each suture system. As shown in FIG. 4, a suture is disposed through the suture aperture. The suture holds the penile tissue and insert together. The suture is then looped around the insert such that the suture is disposed in the suture groove to be flushed with the side edge. The suture is knotted and placed in the suture pocket.

Figure 5:
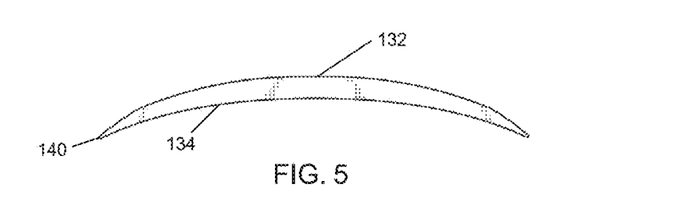
FIG. 5 shows a front view of the embodiment in FIG. 3. The edges of the penile insert are tapered and rounded, i.e. the edges neither sharp nor pointy. Further, the penile insert has a curved shape when viewed from the front.

Referring to FIG. 5, the penile insert has a curved shape. Preferably, the top surface of the penile insert is convexed, and the bottom surface is concaved. This allows for the penile insert to have a curvature similar to that of the penis such that the penile insert can be flushed with the penis without pulling on the penile tissue and causing discomfort to the user.

Figure 7:
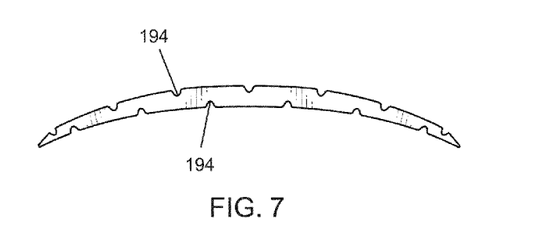
FIG. 7 shows a front view of the embodiment in FIG. 6. Horizontal trenches are disposed on the top and bottom surfaces of the penile insert. Again, the penile insert has a curved shape when viewed from the front.
Figure 8:
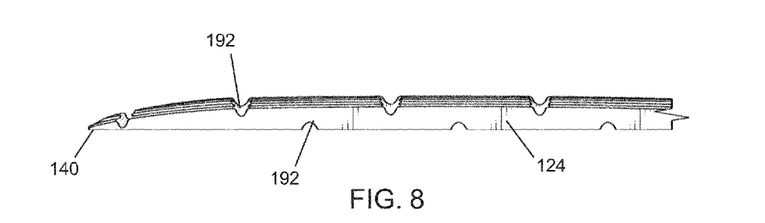
FIG. 8 shows a partial side view of the embodiment in FIG. 6. Vertical trenches are disposed on the top and bottom surfaces of the penile insert.

Further still, the penile insert is rounded and tapered at its edges and distal and proximal ends, as shown in FIGS. 5, 7 and 8. In one embodiment, as shown in FIG. 5, the body may have a maximum depth of about 3-5 mm (e.g. at the apex) and then taper towards at the ends or edges. Preferably, as shown in FIG. 7, the top surface has a downward slope at the ends and edges of the insert such that the ends and edges have rounded tips. The rounded tip may be about 1 mm in height. For example, the top surface may slope down to a 1 mm rounded edge at the distal end of the insert, which is positioned closest to the glans. It is critical that the edges and ends are rounded, and not pointy or sharp, so that a user does not feel a hard edge, thereby ensuring that the insert is comfortable to the user. Further, the tapering of the top surface is advantageous in that it allows for easier insertion of the device into the penis.

In some embodiments, for plateaus that are disposed on the same side edge, a distance between a second corner of a plateau and a first corner of a neighboring plateau, i.e. a width of a valley, is about 5-8 mm. For example, the width of a valley may be about 6 mm. In other embodiments, a distance between two neighboring valleys disposed on the same edge, i.e. a width of a plateau from its first corner to its second corner, is about 6-16 mm. For example, the width of a plateau may be about 8 mm. In still other embodiments, the width of the widest plateau at the distal end or proximal end of the insert may be about 12-16 mm. For instance, the width of the widest plateau may be about 14 mm.

In some embodiments, the valleys may have a "V" shape or a "U" shape. In other embodiments, each valley may have a depth of about 6-10 mm. The depth of the valley is defined as the perpendicular distance between the side edge upon which the valley is disposed and the deepest point of the valley. For example, each valley may have a depth of about 8 mm. In other embodiments, a distance between a valley disposed on the first edge and a neighboring valley disposed on the second edge ranges from about 4 to 6 mm.

In some embodiments, as shown in FIG. 7, the lengthwise trenches may have a "V" shape or a "U" shape. In one embodiment, the lengthwise trenches disposed on the same surface are spaced about 2-3 mm apart from each other. In another embodiment, the top lengthwise trenches and the bottom lengthwise trenches are staggered or misaligned, i.e. the top lengthwise trenches are not aligned with the bottom lengthwise trenches. In yet another embodiment, each lengthwise trench may have a width of about 0.5-1 mm and a depth of about 0.5-1 mm.

Figure 9:
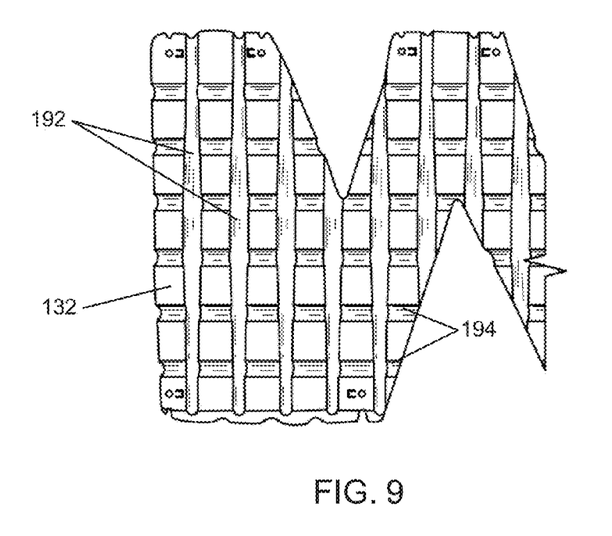
FIG. 9 shows a partial top view of the embodiment in FIG. 6. The top vertical trenches widen at their mid-sections and narrow towards the edges of the penile insert.
Figure 10:
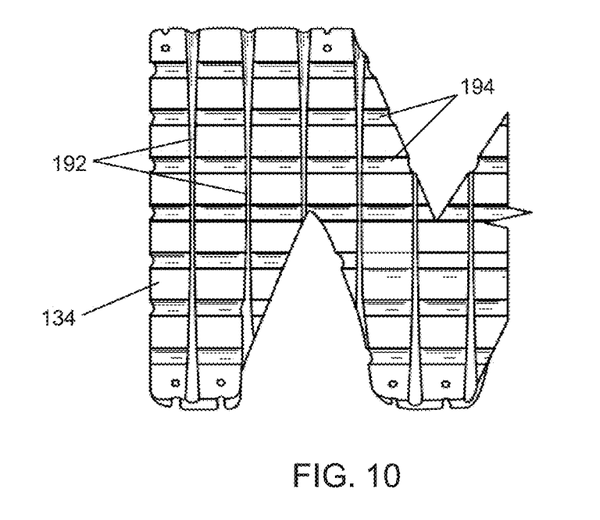
FIG. 10 shows a partial bottom view of the embodiment in FIG. 6. The bottom vertical trenches narrow at their mid-sections and widen towards the edges of the penile insert.

It is to be understood the lengths of the lengthwise trenches will vary along the body due to the zigzag pattern of the body. For example, as shown in FIG. 9-10, the lengths of the lengthwise trenches from the proximal end or the distal end to a valley, or the lengths of the lengthwise trenches from valley to valley are changing since the valleys widen as they approach their respective sides.

In some embodiments, as shown in FIG. 8, the widthwise trenches may have a "V" shape or a "U" shape. The widthwise trenches disposed on the same surface may be spaced about 2-3 mm apart from each other. In other embodiments, the top widthwise trenches and the bottom widthwise trenches are staggered or misaligned, i.e. the top widthwise trenches are not aligned with the bottom widthwise trenches. In further embodiments, each widthwise trench may have a width of about 0.5-1 mm and a depth of about 0.5-1 mm. For example, the maximum width of the widthwise trench is about 1 mm and its minimum width is about 0.5 mm.

It is to be understood the lengths of the widthwise trenches will vary along the body due to the zigzag pattern of the body, which causes the distance between the first and second side to vary. Again, as shown in FIG. 9-10, the lengths of the widthwise trenches at the proximal end and the distal end are longer than the lengths of the widthwise trenches spanning between the plateaus and valleys.

When the penile insert is implanted into a penis, the penile insert can bend upwardly or downwardly. Referring to FIG. 9, when the penile insert is bent, the widthwise trenches at the top surface can close, i.e. their internal walls will approximate, to allow for the insert to flex as needed. However, this approximation is not uniform due to the curvature of the top and bottom surfaces, which causes the central or mid-section of the trench to touch or approximate sooner. Hence, in some embodiments, the top widthwise trenches are wider at the mid-sections so that when the insert is bent, each trench will collapse evenly upon its walls. This widening applies to the top vertical trenches. In other embodiments, as shown in FIG. 10, since the section of the widthwise trench at or near the edges will tend to approximate sooner than at the mid-sections, the bottom widthwise trenches are narrower at their mid-sections and wider at or near the edges to allow for uniform approximation. In still other embodiments, the lengthwise trenches at the top and bottom surfaces have uniform width along their entire lengths.

In alternate embodiments, the body can be without suture apertures, suture grooves, or suture pockets. In this alternative embodiment, the body may be sewn or attached to the tunica albuginea or other tissue layer of the penis by wrapping or tying sutures around the plateaus, by stapling the body to the various tissue layers of the penis, by gluing the body to the various tissue layers of the penis, or the like. In another alternative embodiment, the body may have suture apertures, but without suture grooves or suture pockets.

According to some embodiments, the present invention features a method of increasing a length of a penis in its flaccid or erect state. In one embodiment, the method may comprise implanting, into a shaft of the penis and underneath the penile skin, at least one penile insert device (100) according to any of the embodiments described herein. Preferably, the proximal end (112) may be disposed near a pubic bone and the distal end (114) may be disposed near a glans coronal rim of the penis. More preferably, the top surface (132) may be biased to face the penile skin while the bottom surface may be biased to face the facial tissue layer of the penis. The curvature of the body (110) can be similar to the surface curvature of the penis. In some embodiments, the device (100) may be attached to penis tissue via sutures which are retained in the suture system. Without wishing to limit the invention to a particular theory or mechanism, the device (100) can prevent or reduce shrinkage and elongate the appearance of the penis in its flaccid state. Moreover, the device can elongate the appearance of the penis in its erect state.

In one embodiment, the step of attaching the device (100) to the facial tissue layer of the penis may comprise looping the suture (178) through the suture aperture (172), tissue layer, and the suture groove (174) such that the suture (178) is flushed with the side edge on which said suture groove (174) is disposed. The suture may be knotted into a suture knot that may then be disposed in the suture pocket (176).

Figure 1B:
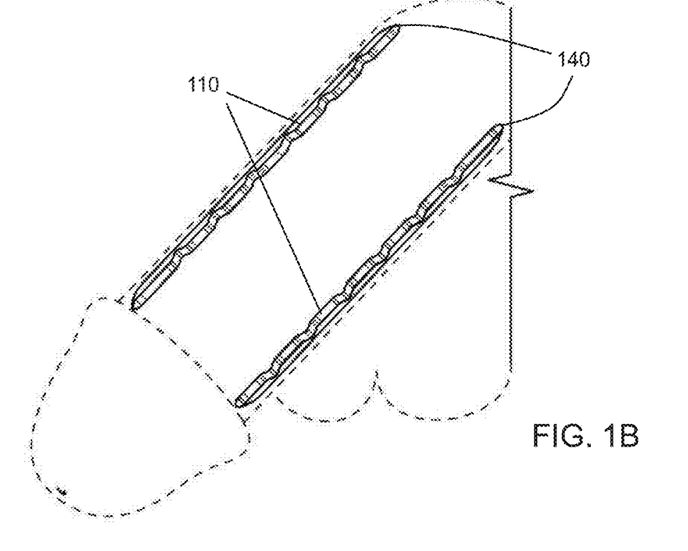
FIG. 1B shows another non-limiting embodiment of the penile insert in-use.
Figure 1C:
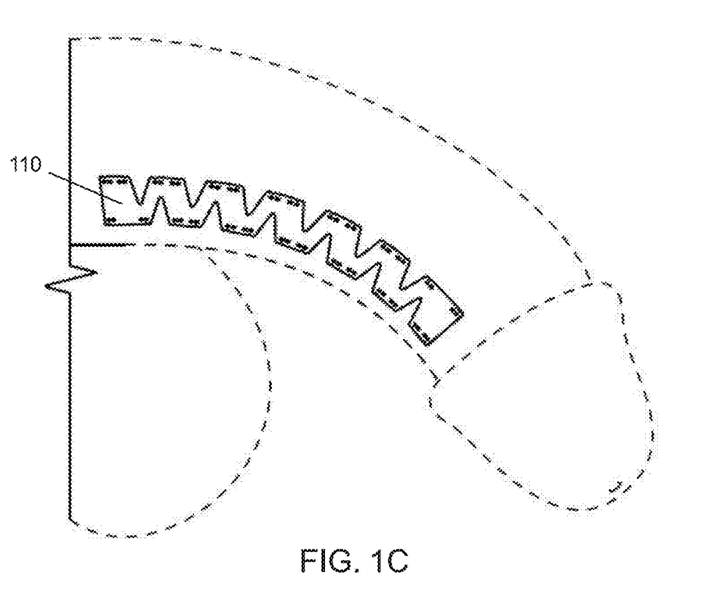
FIG. 1C shows another non-limiting embodiment of the penile insert in-use.
Figure 2A:
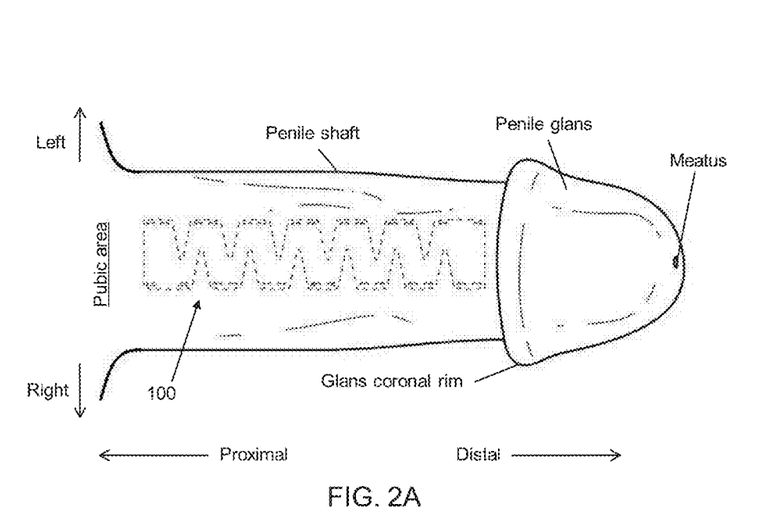
FIG. 2A shows a top view of a penis with the penile insert disposed therein at a dorsal position.
Figure 2B:
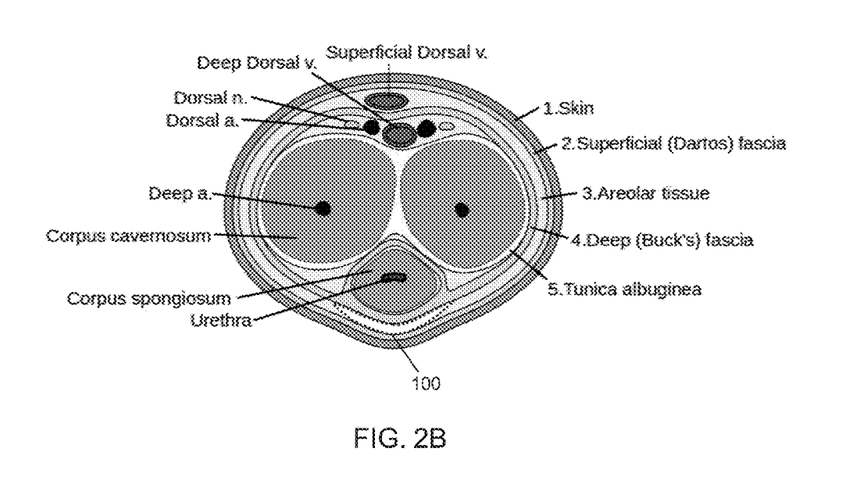
FIG. 2B shows a front cross-sectional view of the penis with the penile insert disposed therein at a ventral position.

In some embodiments, one penile insert device may be implanted into the penile shaft at a dorsal (FIG. 2A) or ventral position (FIG. 2B). In one embodiment, the device (100) can be implanted into the penile shaft at a 12 o'clock position. In another embodiment, the device (100) can be implanted into the penile shaft at a 6 o'clock position. In other embodiments, two devices (100) may be implanted into the penile shaft, as shown in FIG. 1B. The first device (100) may be positioned at a right side of the penis or at about a 3-4 o'clock position, and the second device (100) may be positioned at a left side of the penis or at about an 8-9 o'clock position. In further embodiments, the device (100) may be attached to a facial layer of the Buck's fascia and tunica albuginea.

EXAMPLES

Non-limiting examples of surgical procedures to implant the penile implant device (100) of the present invention are described as follows. Equivalents or substitutes are within the scope of the present invention.

Example 1

Referring to FIG. 1B, two sets of incisions are made through the penile skin and collies fascia. The first set is positioned at about the 3-4 o'clock position and the second set is positioned at about the 8-9 o'clock position. Each set comprises two incisions, one on the distal end of penile shaft, and one on the proximal end of penile shaft. A retractor holds open each incision site for direct viewing and increasing the visual work field. Each incision is made down to the Buck's fascia facial layer, at which point a dilator is inserted through one incision and out the other to create a path for the insertion of the penile implant device (100). The penile implant device (100) is then placed through this path or "tunnel," and the penile implant device (100) is then sutured or otherwise attached to the facial layers of the Buck's fascia and tunica albuginea, both at the proximal incision site, and the distal incision site, while the penile shaft is being pulled or stretched to an extended state. The incision sites are then closed with sutures or other appropriate means, such as staples, glue, or the like.

Example 2

Figure 1A:
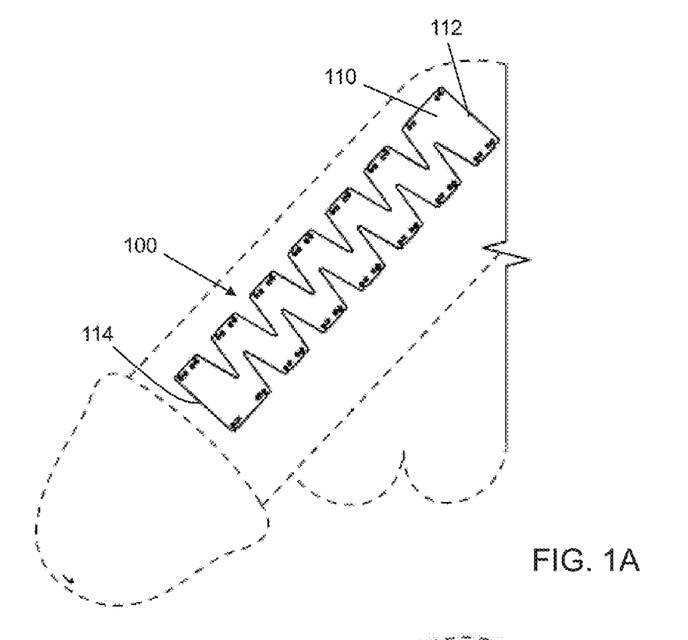
FIG. 1A shows a non-limiting embodiment of the penile insert in-use.

Referring to FIG. 1A, two incisions are made through the penile skin and collies fascia, one on the distal end of penile shaft, and one on the proximal end of penile shaft, both at the "12 o'clock" position of the penile shaft. A retractor holds open the incision site for direct viewing and increasing the visual work field. Each incision is made down to the Buck's fascia facial layer, at which point a dilator is inserted through one incision and out the other to create a path for the insertion of the penile implant device (100). The penile implant device (100) is then placed through this path or "tunnel," and the penile implant device (100) is then sutured or otherwise attached to the facial layers of the Buck's fascia and tunica albuginea, both at the proximal incision site, and the distal incision site, while the penile shaft is being pulled or stretched to an extended state. Both incision sites are then closed with sutures or other appropriate means, such as staples, glue, or the like.

As used herein, the term "about" refers to plus or minus 10% of the referenced number.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

The reference numbers recited in the below claims are solely for ease of examination of this patent application, and are exemplary, and are not intended in any way to limit the scope of the claims to the particular features having the corresponding reference numbers in the drawings.

What is claimed is:

1. A penile insert device (100) effective for increasing a length of a penis in its flaccid or erect state, the penile insert device (100) having an elongated body (110), said elongated body (110) comprising:
   a. a proximal end (112);
   b. a distal end (114);
   c. a first side edge (122);
   d. a second side edge (124);
   e. a top surface (132) fluidly connecting said proximal end (112) to said distal end (114), and said first side edge (122) to said second side edge (124); and
   f. a bottom surface (134) fluidly connecting said proximal end (112) to said distal end (114), and said first side edge (122) to said second side edge (124), wherein the top surface (132) is convexed and the bottom surface (134) is concaved such that the body (110) has a curvature when viewed from the proximal or distal end, wherein each of the first and second side edges (122, 124) is formed by a plurality of alternating lateral plateaus (150) and lateral valleys (160), wherein said lateral plateaus (150) are smoothly connected to adjacent lateral plateaus (150) by said lateral valleys (160), wherein the lateral valleys (160) of the first side edge (122) are staggered with respect to the lateral valleys (160) of the second side edge (124) such that the lateral plateaus and valleys of the first side edge (122) and the lateral plateaus and valleys of the second side edge (124) form a zigzag pattern in the body (110), wherein each lateral plateau (150) comprises two rounded corners (155), each rounded corner (155) smoothly transitioning the lateral plateau (150) into a lateral valley (160), wherein a suture system (170) is disposed on each corner (155) of the lateral plateau, wherein the suture system (170) comprises:
      i. a suture aperture (172) disposed through the body (110) from the top surface (132) to the bottom surface (134);
      ii. a suture groove (174) disposed on the side edge and in alignment with the suture aperture (172); and
      iii. a suture pocket (176) disposed on the top surface (132) adjacent to the suture aperture (172);
   wherein the device (100) is configured to be implanted into a penile shaft of the penis underneath a penile skin such that the proximal end (112) is disposed near a pubic bone and the distal end (114) is disposed near a glans coronal rim of the penis, wherein the curvature of the body (110) is similar to a surface curvature of the penis, wherein the suture system (170) is configured to retain a suture (178) that sutures the device (100) to a penile facial tissue layer,
   wherein the device (100) prevents or reduces shrinkage and elongates an appearance of the penis in its flaccid state, and wherein the device (100) elongates the appearance of the penis in its erect state.

2. The penile insert device (100) of claim 1, wherein the top surface (132) tapers at the proximal and distal ends and at the first and second side edges.

3. The penile insert device (100) of claim 1, wherein the proximal and distal ends have rounded tips (140), and wherein the first and second side edges have rounded tips (140).

4. The penile insert device (100) of claim 1, wherein when attaching the device (100) to the penile facial tissue layer, the suture (178) is disposed through the suture aperture (172) and penile facial tissue layer and looped around the side edge, wherein the suture (178) is disposed in the suture groove (174) such that the suture (178) is flushed with the side edge, wherein the suture is knotted into a suture knot that is disposed in the suture pocket (176).

5. The penile insert device (100) of claim 1, wherein the body (110) is constructed from a semi-rigid, bendable, medical-grade silicone rubber material.

6. The penile insert device (100) of claim 1, wherein the elongated body (110) further comprises a plurality of widthwise trenches (192) disposed on the top and bottom surfaces, and extending from the first side edge (122) to the second side edge (124), and a plurality of lengthwise trenches (194) disposed on the top and bottom surfaces, wherein the lengthwise trenches (194) are perpendicular to the widthwise trenches (192).

7. The penile insert device (100) of claim 6, wherein each widthwise trench (192) disposed on the top surface (132) gradually widens midway between the first side edge (122) and the second side edge (124).

8. The penile insert device (100) of claim 6, wherein each widthwise trench (192) disposed on the bottom surface (132) gradually narrows midway between the first side edge (122) and the second side edge (124).

9. A method of increasing a length of a penis in its flaccid or erect state, said method comprising:
   a. implanting at least one penile insert device (100) according to claim 1 into the penile shaft underneath the penile skin such that the proximal end (112) is disposed near the pubic bone and the distal end (114) is disposed near the glans coronal rim of the penis, wherein the top surface (132) is biased to face the penile skin while the bottom surface is biased to face the facial tissue layer of the penis, wherein the curvature of the body (110) is similar to the surface curvature of the penis; and
   b. attaching the device (100) to the facial tissue layer via sutures that are retained in the suture system (170);
   wherein the device (100) prevents or reduces shrinkage and elongates the appearance of the penis in its flaccid state, and wherein the device (100) elongates the appearance of the penis in its erect state.

10. The method of claim 9, wherein attaching the device (100) to the facial tissue layer of the penis comprises looping the suture (178) through the suture aperture (172), tissue layer, and the suture groove (174) such that the suture (178) is flushed with the side edge on which said suture groove (174) is disposed, wherein the suture is knotted into a suture knot that is disposed in the suture pocket (176).

11. The method of claim 9, wherein one penile insert device is implanted into the penile shaft at a dorsal or ventral position.

12. The method of claim 9, wherein two devices (100) are implanted into the penile shaft, wherein the first device (100) is positioned at a left side of the penis and the second device (100) is positioned at a right side of the penis.

13. The method of claim 9, wherein the device (100) is attached to the facial layer of a Buck's fascia and tunica albuginea.

14. A penile insert device (100) effective for increasing a length of a penis in its flaccid or erect state, the penile insert device (100) having an elongated body (110), said elongated body (110) comprising:
   a. a proximal end (112);
   b. a distal end (114);
   c. a first side edge (122);
   d. a second side edge (124);
   e. a top surface (132); and
   f. a bottom surface (134),
      wherein each of the first and second side edges (122, 124) is formed by a plurality of alternating lateral plateaus (150) and lateral valleys (160), wherein said lateral plateaus (150) are smoothly connected to adjacent lateral plateaus (150) by said lateral valleys (160),
      wherein the lateral valleys (160) of the first side edge (122) are staggered with respect to the lateral valleys (160) of the second side edge (124) such that the lateral plateaus and valleys of the first side edge (122) and the lateral plateaus and valleys of the second side edge (124) form a zigzag pattern in the body (110), wherein each lateral plateau (150) comprises two rounded corners (155), each rounded corner (155) smoothly transitioning the lateral plateau (150) into a lateral valley (160);
   wherein the device (100) is configured to be implanted into a penile shaft underneath a penile skin and attached to a penile facial tissue layer, wherein the device (100) prevents or reduces shrinkage and elongates an appearance of the penis in its flaccid state, and wherein the device (100) elongates the appearance of the penis in its erect state.

15. The penile insert device (100) of claim 14, wherein the device (100) is configured to be implanted into the penile shaft such that the proximal end (112) is disposed near a pubic bone and the distal end (114) is disposed near a glans coronal rim of the penis, wherein the elongated body (110) has a curvature that is similar to a surface curvature of the penis.

16. The penile insert device (100) of claim 14, wherein a suture system (170) is disposed on each corner (155) of the lateral plateau, wherein the suture system (170) comprises a suture aperture (172) disposed through the body (110) from the top surface (132) to the bottom surface (134).

17. The penile insert device (100) of claim 16, wherein when the device (100) is attached to the penile facial tissue layer, a suture (178) is looped through the suture aperture, facial tissue layer, and around the side edge.

18. The penile insert device (100) of claim 17, wherein the suture system (170) further comprises a suture groove (174) disposed on the side edge and in alignment with the suture aperture (172), wherein the suture (178) is configured to be disposed in the suture groove (174) such that the suture (178) is flushed with the side edge.

19. The penile insert device (100) of claim 18, wherein the suture system (170) further comprises a suture pocket (176) disposed on the top surface (132) adjacent to the suture aperture (172), wherein the suture is configured to be knotted into a suture knot and disposed in the suture pocket (176).

20. The penile insert device (100) of claim 16, wherein the elongated body (110) further comprises a plurality of widthwise trenches (192) disposed on the top and bottom surfaces, and extending from the first side edge (122) to the second side edge (124), and a plurality of lengthwise trenches (194)

disposed on the top and bottom surfaces, wherein the lengthwise trenches (194) are perpendicular to the widthwise trenches (192).

\* \* \* \* \*